(12) United States Patent
Pierik et al.

(10) Patent No.: US 9,657,338 B2
(45) Date of Patent: May 23, 2017

(54) METHOD FOR IMMOBILIZING NUCLEIC ACIDS ON A SUPPORT

(75) Inventors: Anke Pierik, Eindhoven (NL); Hendrik Roelof Stapert, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 1254 days.

(21) Appl. No.: 13/121,206

(22) PCT Filed: Sep. 22, 2009

(86) PCT No.: PCT/IB2009/054151
§ 371 (c)(1),
(2), (4) Date: Mar. 28, 2011

(87) PCT Pub. No.: WO2010/038170
PCT Pub. Date: Apr. 8, 2010

(65) Prior Publication Data
US 2011/0319275 A1    Dec. 29, 2011

(30) Foreign Application Priority Data

Oct. 1, 2008 (EP) .................................... 08165578

(51) Int. Cl.
C12Q 1/68 (2006.01)
C12P 19/34 (2006.01)
C07H 21/02 (2006.01)
C07H 21/04 (2006.01)

(52) U.S. Cl.
CPC ................................. C12Q 1/6837 (2013.01)

(58) Field of Classification Search
USPC ..... 435/6.1, 6.11, 91.1, 283.1, 287.1, 287.2; 436/94, 501; 536/23.1, 24.3
See application file for complete search history.

(56) References Cited

U.S. PATENT DOCUMENTS

| 4,889,606 | A * | 12/1989 | Dyson et al. ................ 204/464 |
| 6,653,473 | B2 | 11/2003 | Reed et al. |
| 7,041,445 | B2 | 5/2006 | Chenchik et al. |
| 2002/0077471 | A1 * | 6/2002 | Mulligan et al. ............ 536/25.4 |

FOREIGN PATENT DOCUMENTS

| WO | 8911548 | 11/1989 |
| WO | 03039703 A2 | 5/2003 |
| WO | 2006024314 A1 | 3/2006 |

OTHER PUBLICATIONS

Colony Lifts Using Immobilon™-NY+Membrane. Technical Note from Millipore, pp. 1-10, published on Nov. 15, 1999.*
Petrovykh et al., Quantitative Analysis and Characterization of DNA Immobilized on Gold. J. Am. Chem. Soc., 125, 5219-5226, 2003.*
The definition of "peptide nucleic acid" from Wikipedia, the free encyclopedia. Printed on May 13, 2013.*
Boiteux et al., Coding Properties of Poly( deoxycytidylic acid) Templates Containing Uracil or Apyrimidinic Sites: In Vitro Modulation of Mutagenesis by Deoxyribonucleic Acid Repair Enzymes. Biochemistry, 21, 6746-6751,1982.*
By Nakano K et al; "Photoactive, Covalent Attchment of Deoxyribonucleic Acid on Gold With Double-Strand Specificity Using Self-Assembled Monolayers Containing Psoralen"; Amsterdam, NL, vol. 578, No. 1, Sep. 18, 2006, pp. 93-99, XP025047796 ISSN: 0003-2670 [retrieved on Sep. 18, 2006]; Retrieved on line: at sciencedirect.com.
By C. Lauted et al.; "POSaM: A Fast Flexible, Open-Source, Inkjet Oligonucleotide Synthesizer and Microarrayer" Genome Biology, Biomed Central Ltd., London, GB, vol. 5, no. Issue 8, Jul. 27, 2004, pp. R58.3, XP021012917 ISSN: 1465-6906 the whole document.
By Saiki R K et al: "Genetic Analysis of Amplified DNA With Immobilized Sequencespecific Oligonucleotide Probes" Proceedings of the National Academy of Sciences of USA, National Academy of Science, Washington, DC, US, vol. 86, No. 16, Aug. 1, 1989; pp. 6230-6234, XP000268602 ISSN: 0027-8424 the whole document.
By Mocanu D et al: "Quantitative Analysis of DNA Hybridization in a Flowthrough Microarray for Molecular Testing" Analytical Biochemistry, Academic Press Inc, New York, vol. 380, No. 1, Sep. 1, 2008, pp. 84-90, XP022832102 ISSN: 0003-2697 [retrieved on May 27, 2008] abstract.
By Cole et al: "Psoralen Monoadducts and Interstrand Cross-Links in DNA DNA" Biqchimica Et Biophysica Acta, N. Nucleic Acids and Proteinsythesis, Amsterdam, NL, vol. 254, No. 1, Nov. 29, 1971, pp. 30-39, XP023371230 ISSN: 0005-2787 [retrieved on Nov. 29, 1971] the whole document.
By A.C. Pease "Light-Generated Oligonucleotide Arrays for Rapid DNA Sequence Analysis"; Biochemistry; Communicated by Ronald (Continued)

Primary Examiner — Frank Lu (57) ABSTRACT

The present invention relates to a method for immobilizing nucleic acids on a support, comprising the provision of a nucleic acid with a stretch of nucleotides of only one basetype and the immobilization of said nucleic acid on a support by crosslinking by light, wherein said crosslinking by light is performed at a wavelength of about 300-500 nm, preferably at a wavelength of 365 nm. The present invention further relates to a method for the analysis of nucleic acids immobilized according to the invention, which comprises the hybridization of the immobilized nucleic acid with complementary and mismatch segments. Furthermore, the present invention relates to immobilized nucleic acids obtainable by the method of the invention, the use of accordingly immobilized nucleic acids for the production of nucleic acid arrays and a diagnostic kit, comprising an array of nucleic acids which are immobilized according to the present invention.

14 Claims, 5 Drawing Sheets

(56) References Cited

OTHER PUBLICATIONS

W. Davis, Jan. 4, 1994; Proc. Natl. Acad. Sci. USA 91 (1994); pp. 5022-5026.

* cited by examiner

METHOD FOR IMMOBILIZING NUCLEIC ACIDS ON A SUPPORT

FIELD OF THE INVENTION

The present invention relates to a method for immobilizing nucleic acids on a support, comprising the provision of a nucleic acid with a stretch of nucleotides of only one basetype and the immobilization of said nucleic acid on a support by crosslinking by light, wherein said crosslinking by light is performed at a wavelength of about 300-500 nm, preferably at a wavelength of 365 nm.

The present invention further relates to a method for the analysis of nucleic acids immobilized according to the invention, which comprises the hybridization of the immobilized nucleic acid with a probe comprising a complementary segment, a probe comprising a single mismatch segment, a probe comprising a double mismatch segment and/or a probe comprising a segment carrying a higher number of mismatches and the subsequent determination of the melting point of the hybrids which have been formed between the immobilized nucleic acid and the hybridization probes.

Furthermore, the present invention relates to immobilized nucleic acids obtainable by the method of the invention, the use of accordingly immobilized nucleic acids for the production of nucleic acid arrays and a diagnostic kit, comprising an array of nucleic acids which are immobilized according to the present invention.

BACKGROUND OF THE INVENTION

Biochips or biological microarrays, in particular DNA microarrays, have become an important tool in modern molecular biology and medicine. Typically the chips consist of an arrayed series of a large number of microscopic spots of nucleic acid molecules, each containing small amounts of a specific nucleic acid sequence. This can be, for example, a short section of a gene or other DNA element that are used as capture probes to hybridize a cDNA or cRNA sample (a target or target probe) under conditions, which allow a binding between the capture probe and the corresponding target. Capture probe-target hybridization is typically detected and quantified by fluorescence-based detection of fluorophore-labeled targets to determine relative abundance of nucleic acid sequences in the target.

Microarray technology evolved from Southern blotting, where fragmented DNA is attached to a substrate and then probed with a known gene or fragment. The use of a collection of distinct DNAs in arrays for expression profiling was first described in 1987, and the arrayed DNAs were used to identify genes whose expression is modulated by interferon. These early gene arrays were made by spotting cDNAs onto filter paper with a pin-spotting device. The use of miniaturized microarrays, in particular for gene expression profiling was first reported in the 1990s. A complete eukaryotic genome on a microarray was published in 1997.

A variety of technologies may be used in order to fabricate such microarrays. The techniques include printing with fine-pointed pins, photolithography using pre-made masks, photolithography using dynamic micromirror devices, ink-jet printing (Lausted C et al., 2004, Genome Biology 5: R58), or electrochemistry.

The photolithographic technique is directed to the production of oligonucleotide arrays by synthesizing the sequences directly onto the array surface. The technique involves photolithographic synthesis on a silica substrate where light and light-sensitive masking agents are utilized to generate a sequence one nucleotide at a time across the entire array (Pease et al., 1994, *PNAS* 91: 5022-5026). Each applicable probe is selectively unmasked prior to bathing the array in a solution of a single nucleotide, then a masking reaction takes place and the next set of probes are unmasked in preparation for a different nucleotide exposure. After several repetitions, the sequences of every probe become fully constructed. Accordingly constructed oligonucleotides may be longer (e.g. 60-mers) or shorter (e.g. 25-mers) depending on the desired purpose.

In spotted microarrays, the oligonucleotide probes are deposited as intact sequences, i.e. the probes are synthesized prior to deposition on the array surface and are then spotted onto the substrate. A common approach utilizes an array of fine pins or needles controlled by a robotic arm that is dipped into wells containing DNA probes and then depositing each probe at designated locations on the array surface, or an ink jet printing device, which deposits the probe material via the ejection of droplets. The resulting array of probes represents the nucleic acid profiles of the prepared capture probes and can interact with complementary cDNA or cRNA target probes, e.g. derived from experimental or clinical samples. In addition, these arrays may be easily customized for specific experiments, since the probes and printing locations on the arrays can be chosen specifically.

Central to several of these techniques is the efficient immobilization of the nucleic acid onto the support or material. A classical way of immobilizing nucleic acids on a support is the application of UV-light, i.e. UV-crosslinking. Church and Gilbert described 1984 that the application of UV light of a wavelength of 254 nm leads to the immobilization of DNA fragments to nylon filters (Church and Gilbert, PNAS, 1984, 81, p: 1991-1995). An advanced version of this approach was proposed by Saiki et al., PNAS, 1989, 86, p: 6230-6234, which described that oligonucleotides comprising poly(dT) tails could more readily be fixated to membranes when using UV-light of a wavelength of 254 nm. The effect was attributed to a more efficient binding of light-activated thymine bases to a membrane.

However, irradiating nucleic acids with short wavelength UV-light of around 254 nm typically leads to severe damages to the nucleic acid molecule, which may have consequences for the capability of the molecules to hybridize with complementary sequences and could thus compromise their usability in microarray systems. In particular, such an irradiation may lead to the generation of pyrimidine dimers due to the establishment of cyclobutan rings between adjacent pyrimidines, in particular between neighboring thymine residues. A further effect may be the generation of associations between adjacent thymine and cytosine residues, resulting in TC(6,4)-products.

There is, thus, a need for an alternative immobilization method for nucleic acids which allows an efficient fixation of the nucleic acid on a support that overcomes the disadvantageous damages to the molecules accompanied with a traditional UV-crosslinking at around 254 nm.

OBJECTS AND SUMMARY OF THE INVENTION

The present invention addresses this need and provides means and methods which allow an efficient immobilization of nucleic acids and concomitantly minimizes damages in the nucleic acid molecule during such an immobilization process.

The above objective is accomplished by a method for immobilizing nucleic acids on a support by using a longer wavelength of about 300-500 nm, which reduces damages in the nucleic acid molecule during the crosslinking process. Particularly, the objective is accomplished by a method comprising the provision of a nucleic acid with a stretch of nucleotides of only one basetype and the immobilization of said nucleic acid on a support by crosslinking by light, wherein said crosslinking by light is performed at a wavelength of about 300-500 nm, preferably at a wavelength of 365 nm.

It is an advantage of the method according to the present invention that the deleterious effects of low wavelength UV-radiation during immobilization processes can be avoided while the nucleic acids are still efficiently immobilized onto appropriate support material or substrates. It has been found by the present inventors that nucleotides or stretches of nucleotides of only one basetype can be immobilized on support material not only by UV-crosslinking at a wavelength of 254 nm, but also at higher wavelengths of more than 300 nm, particularly at a wavelength of 365 nm. Since light of a wavelength above 300 nm conveys much lower energy doses per photon than the traditionally used short wavelength UVC radiation, such long wavelength light is generally considered to cause no or a drastically reduced number of damages to nucleic acid molecules. This effect is apparently associated with the molecular influence of the radiation on pyrimidine residues, in particular on thymines. Thus in contrast to the traditional UV-crosslinking approach, which was based on the effect of short wavelength UV-light primarily on thymidines and nolens volens accepted the deleterious consequences on the structure and function of the treated nucleic acid molecules for the sake of an efficient immobilization, the approach of the present invention relies on a different mechanism that conveys an interaction between structural elements in the support material and bases which are primarily different from thymine, in particular guanine and uracil, leading to an effectual and stable immobilization of the nucleic acid molecules. Thereby damages to the nucleic acid molecule can be avoided. This in turn may advantageously be used for the preparation of microarray systems since correspondingly immobilized nucleic acids show an elevated interaction behavior with complementary probes and accordingly contribute to an improvement of the signal retrieval and signal evaluation during the microarray operation. Furthermore, the present invention may advantageously be used for a differential immobilization approach, which makes use of light of two distinct wavelengths and correspondingly reactive nucleotides. Such an approach may be helpful during the production of microarray systems or may be used for the establishment of different immobilization pattern for scientific purposes.

In a preferred embodiment of the present invention, the nucleic acid to be immobilized is DNA, RNA, PNA, CNA, HNA, LNA or ANA an oligonucleotide thereof or any combination thereof.

In a further preferred embodiment of the present invention, said nucleic acid as mentioned above is a double-stranded or single-stranded molecule.

In another preferred embodiment of the present invention, said stretch of nucleotides of one base type included in the nucleic acids to be immobilized is a stretch of guanines or uracils. In a particularly preferred embodiment of the present invention said stretch of nucleotides of only one basetype is a stretch of guanines.

In a further preferred embodiment of the present invention, said stretch of nucleotides of only one basetype has a length from about 7 to about 100 nucleotides. In a particularly preferred embodiment said stretch of nucleotides has a length of about 16 nucleotides.

In yet another preferred embodiment of the present invention, said stretch of nucleotides of only one basetype is located at the 3' or 5' terminus of said nucleic acid.

In a further preferred embodiment of the present invention, the nucleic acid to be immobilized according to the invention is represented by the following formula:

$$5'\text{-}Y_n\text{—}X_m\text{—}B_r\text{—}X_p\text{—}Z_q\text{-}3'$$

with Y and Z being stretches of nucleotides of only one basetype, wherein Y and Z can be of the same or of a different basetype; X being a spacer, preferably composed of abasic nucleotides; B being a sequence of more than one basetype and n, m, r, p and q being the numbers of nucleotides in the nucleic acid, wherein the following conditions may apply: n, m, p, q, r>1; n, m, r>1 and p, q=0; p, q, r>1 and n, m=0; n, q, r>1 and m, p=0; n, r>1 and m, p, q=0; q, r>1 and n, m, p=0.

In another preferred embodiment of the present invention, the crosslinking by light as defined herein above is performed using an amount of energy ranging from about 0.5 Joule/cm² to about 10 Joule/cm².

In a further preferred embodiment of the present invention, said solid support as mentioned above comprises amine-functionalized groups.

In another preferred embodiment of the present invention, said solid support as mentioned above or said support comprising amine-functionalized groups comprises primary or secondary amines. In another, related preferred embodiment of the present invention said solid support as mentioned above or said support comprising amine-functionalized groups may also or alternatively comprise psoralen.

In a further particularly preferred embodiment of the present invention, said amine-functionalized groups comprising support comprises a porous substrate. In an even more preferred embodiment said above mentioned porous substrate is composed of nylon.

In a further particularly preferred embodiment of the present invention, said amine-functionalized groups comprising support comprises a non-porous substrate. In an even more preferred embodiment of the present invention said above mentioned non-porous substrate is composed of glass, poly-L-lysine coated material, nitrocellulose, polystyrene, cyclic olefin copolymer (COC), cyclic olefin polymer (COP), polypropylene, polyethylene or polycarbonate.

In another aspect the present invention relates to a method for the analysis of a nucleic acid, which is immobilized according to the invention, which comprises the steps of hybridizing said immobilized nucleic acid with at least one polynucleotide hybridization probe comprising a segment which is complementary to a region of said immobilized nucleic acid and at least one nucleic acid hybridization probe comprising a segment which carries a single mismatch in comparison to a region of said immobilized nucleic acid; and/or a least one nucleic acid hybridization probe comprising a segment which carries a double mismatch in comparison to a region of said immobilized nucleic acid and/or a least one nucleic acid hybridization probe comprising a segment which carries a higher number of mismatches; and determining the melting point of the hybrids which have been formed between the immobilized nucleic acid and said hybridization probe(s), wherein the melting point is correlated with the type and/or number of mismatches present in the nucleic acid hybridization probe and the number of nucleotides of only one basetype within the stretch of nucleotides of only one basetype.

In another aspect the present invention concerns immobilized nucleic acids which are obtainable by a method according to method of the present invention, as defined herein above.

In yet another aspect the present invention relates to the use of nucleic acids, which are immobilized according to the present invention, for the production of a nucleic acid array.

In yet a further aspect the present invention relates to a diagnostic kit, comprising an array of nucleic acids which are immobilized according to the method of the present invention, as defined herein above, and a control probe containing a defined amount of a known, labeled nucleic acid complementary to at least one of said immobilized nucleic acids.

These and other characteristics, features and objectives of the present invention will become apparent from the following detailed description, taken in conjunction with the accompanying figures and examples, which demonstrate by way of illustration the principles of the invention. The description is given for the sake of example only, without limiting the scope of the invention.

DETAILED DESCRIPTION OF THE INVENTION

The inventors have found that stretches of nucleotides of only one basetype can be immobilized on support material by crosslinking by light at a wavelength of 300-500 nm, particularly at a wavelength of 365 nm.

Although the present invention will be described with respect to particular embodiments, this description is not to be construed in a limiting sense.

Before describing in detail exemplary embodiments of the present invention, definitions important for understanding the present invention are given.

As used in this specification and in the appended claims, the singular forms of "a" and "an" also include the respective plurals unless the context clearly dictates otherwise.

In the context of the present invention, the terms "about" and "approximately" denote an interval of accuracy that a person skilled in the art will understand to still ensure the technical effect of the feature in question. The term typically indicates a deviation from the indicated numerical value of ±20%, preferably ±15%, more preferably ±10%, and even more preferably ±5%.

It is to be understood that the term "comprising" is not limiting. For the purposes of the present invention the term "consisting of" is considered to be a preferred embodiment of the term "comprising of". If hereinafter a group is defined to comprise at least a certain number of embodiments, this is meant to also encompass a group which preferably consists of these embodiments only.

Furthermore, the terms "first", "second", "third" or "(a)", "(b)", "(c)", "(d)" etc. and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

In case the terms "first", "second", "third" or "(a)", "(b)", "(c)", "(d)" etc. relate to steps of a method or use there is no time or time interval coherence between the steps, i.e. the steps may be carried out simultaneously or there may be time intervals of seconds, minutes, hours, days, weeks, months or even years between such steps, unless otherwise indicated in the application as set forth herein below.

As has been set out above, the present invention concerns in one aspect a method for immobilizing nucleic acids on a support comprising the provision of a nucleic acid with a stretch of nucleotides of only one basetype and the immobilization of said nucleic acid on a support by crosslinking by light, wherein said crosslinking by light is performed at a wavelength of about 300-500 nm, preferably at a wavelength of 365 nm.

The term "immobilizing a nucleic acid on a support" relates to the association of nucleic acid molecules to a supportive substrate via molecular interactions which position the nucleic acid at a specific area of the supportive substrate and concomitantly impede a detaching of the nucleic acids, e.g. during washing, rinsing or chemical hybridization steps. Typically, such molecular interactions are based on covalent chemical bonds between structural elements or functional groups of the support material and the nucleic acid to be immobilized, e.g. corresponding functional groups of the nucleic acid, as known to the person skilled in the art.

The term "solid support" means that the support material is mainly of non-liquid consistence and thereby allows for an accurate and trackable positioning of the nucleic acid on the support material.

The term "providing a nucleic acid" relates to the supply of a nucleic acid to or into a reaction environment, which constitutes a suitable and adequate ambience for an immobilization reaction. Corresponding environmental parameters relate, for instance, to the temperature, pH or humidity or the presence of specific buffer solutions or additional ingredients, as known to the person skilled in the art. The term "providing" also refers to the initiation of immobilization reactions and deposition of the nucleic acids on a support. Furthermore, the provision of nucleic acids may also comprise any preparatory steps which are necessary for a subsequent successful immobilization procedure. It is known that one key issue associated with the irradiation of support material is their moisture content. Since water absorbs light irradiation, in particular UV irradiation, a variation in the drying process may have influence on the outcome of the crosslinking process. The moisture content of a support material may be adjusted according to any suitable means known to the person skilled in the art. Preferably, the "provision of nucleic acids" may include a pre-drying procedure for a certain period of time in order to adjust the amount of water or liquid present.

The term "stretch of nucleotides of only one basetype" in the context of the present invention relates to a portion of the nucleic acid molecule which is composed of only one base, e.g. thymine, guanine, adenine, cytosine or uracil or any chemical derivative thereof known to the person skilled in the art which is capable of interacting with a complementary base. Said portion of the nucleic acid molecule may have a variable length between only a few bases and more than 100 bases. The term "only one basetype" not only encompasses bases which are identical, but also bases or derivatives thereof which show a comparable chemical behavior in terms of interaction with complementary bases. The term thus relates in the exemplary case of guanines not only to the basetype or nucleotide guanine alone, but also to functionally equivalent derivates or modifications thereof. The term "functionally equivalent" relates to the capability of the base to establish a non-covalent connection with a complementary base, which is chemically similar to the non-covalent connection of the nucleotide or base it is derived from. Such functionally equivalent or modified bases may still be able to perform a hybridization binding with a complementary base.

The term "crosslinking by light" relates to an interaction between said support material and said nucleic acid via the formation of molecular interactions or bonds that link both structural elements together under the influence or driven by the energy provided by the energy source light. Crosslinking by light in the context of the present invention is carried out by applying light of a typical wavelength between about 300 nm and about 500 nm, preferably at 365 nm to nucleic acid molecules in order to induce an interaction between the molecules and support material. Typically, the induced interaction between the molecules and the support material is a covalent binding of the nucleic acid to the material. Crosslinking by light in the range of about 300 nm to about 500 nm may, for example, be carried out by using near or long wave UV light, UVA light or black light. Fundamentally, the linkage proceeds through the bases of a nucleic acid molecule, e.g. guanine, uracil or thymine, and to a certain extent also cytosine or adenine residues, which react with corresponding and suitable functional chemical groups on the support material, as known to the person skilled in the art. The term "range of about 300 nm to about 500 nm" refers to every single wavelength between 300 nm and 500 nm. It preferably also refers to certain subranges thereof, e.g. a subrange of 300 to 320 nm, 320 to 340 nm, 340 to 360 nm, 360 to 380 nm, 380 to 400 nm, 400 to 420 nm, 420 to 440 nm, 440 to 460 nm, 460 to 480 nm, 480 to 500 nm. Typically, a crosslinking performed at wavelength between about 300 nm to about 500 nm may be considered as a non-classical UV- or long wavelength-crosslinking. The wavelength of the light to be used may be determined primarily by the choice of lamps. For instance, in order to establish a wavelength in the spectrum of 300-500 nm a high-pressure mercury UV-lamp may be used. Such a lamp typically emits not only one wavelength, but a spectrum of wavelengths, as the person skilled in the art would know. The term "spectrum of 300-500 nm" relates to such a typical spectrum emitted from a high-pressure mercury UV-lamp. Alternatively, the light may also be emitted from a LED, which may have a different emission spectrum or from any other lamp or light source known to the person skilled in the art as long the majority of the emitted wavelengths are within the range of 300-500 nm.

In a particularly preferred embodiment the prominent emission line is at 365 nm within said emission spectrum of 300-500 nm.

Further preferred is a crosslinking approach in which a light source is used which does not emit an entire spectrum of wavelengths, but only specific wavelengths, particularly preferably a wavelength of 365 nm. Such a confinement may be achieved by using specific lamp or LED models or by employing filter elements which allow solely the passage of defined wavelengths, as the person skilled in the art would know.

The nucleic acid to be immobilized in accordance with a preferred embodiment of the present invention may be DNA, RNA, PNA, CNA, HNA, LNA or ANA. The DNA may be in the form of, e.g. A-DNA, B-DNA or Z-DNA. The RNA may be in the form of, e.g. p-RNA, i.e. pyranosysl-RNA or structurally modified forms like hairpin RNA or a stem-loop RNA.

The term "PNA" relates to a peptide nucleic acid, i.e. an artificially synthesized polymer similar to DNA or RNA which is used in biological research and medical treatments, but which is not known to occur naturally. The PNA backbone is typically composed of repeating N-(2-aminoethyl)-glycine units linked by peptide bonds. The various purine and pyrimidine bases are linked to the backbone by methylene carbonyl bonds. PNAs are generally depicted like peptides, with the N-terminus at the first (left) position and the C-terminus at the right.

The term "CNA" relates to an aminocyclohexylethane acid nucleic acid. Furthermore, the term relates to a cyclopentane nucleic acid, i.e. a nucleic acid molecule comprising for example 2'-deoxycarbaguanosine.

The term "HNA" relates to hexitol nucleic acids, i.e. DNA analogues which are built up from standard nucleobases and a phosphorylated 1,5-anhydrohexitol backbone.

The term "LNA" relates to locked nucleic acids. Typically, a locked nucleic acid is a modified and thus inaccessible RNA nucleotide. The ribose moiety of an LNA nucleotide may be modified with an extra bridge connecting the 2' and 4' carbons. Such a bridge locks the ribose in a 3'-endo structural conformation. The locked ribose conformation enhances base stacking and backbone pre-organization. This may significantly increase the thermal stability, i.e. melting temperature of the oligonucleotide.

The term "ANA" relates to arabinoic nucleic acids or derivatives thereof. A preferred ANA derivative in the context of the present invention is a 2'-deoxy-2'-fluoro-beta-D-arabinonucleoside (2'F-ANA).

In a further preferred embodiment nucleic acid molecules may comprise a combination of any one of DNA, RNA, PNA, CNA, HNA, LNA and ANA. Particularly preferred are mixtures of LNA nucleotides with DNA or RNA bases.

In a further preferred embodiment the nucleic acid molecules as defined herein above may be in the form of short oligonucleotides, long oligonucleotides or polynucleotides.

In another preferred embodiment the nucleic acid molecules as defined herein above may be single-stranded or double-stranded. The term "single-stranded nucleic acid" relates to nucleic acid molecules which comprise a single sugar-phosphate backbone and/or are not organized in a helical form. Preferably these nucleic acid molecules exhibit no secondary structures or intermolecular associations. The term "double stranded nucleic acid" relates to nucleic acid molecules which comprise two sugar-phosphate backbones. In a preferred embodiment the double-stranded nucleic acids are organized in a double helical form. In a further preferred embodiment double-stranded nucleic acids according to the present invention may be composed of different types of nucleic acid molecules, e.g. of DNA and RNA, DNA and PNA, DNA and CNA, DNA and HNA, DNA and LNA, DNA and ANA, or RNA and CNA, RNA and PNA, RNA and CNA, RNA and HNA, RNA and LNA, RNA and ANA, or PNA and CNA, PNA and HNA, PNA and LNA, PNA and ANA or CNA and HNA, CNA and LNA, CNA and ANA, or HNA and LNA, HNA and ANA, or LNA and ANA. They may alternatively also be composed of combinations of stretches of any of the above mentioned nucleotide variants.

In a further preferred embodiment of the present invention crosslinking of nucleic acids at a wavelength of 300-500 nm, in particular at 365 nm may be used in order to immobilize nucleic acid molecules comprising guanine, uracil or thymine nucleotides, more preferably nucleic acids comprising a stretch of only one base type composed of guanine or uracil nucleotides. In a more preferred embodiment, said stretch of only one base type is composed of guanine bases, since it has been found by the present inventors that a stretch of only one base type composed of guanine may be immobilized more efficiently to a support material at a wavelength of 365 nm than a stretch of only one base type composed of uracil, which in turn may be immobilized more efficiently to a support material at said wavelength than a stretch of only one base type composed of thymine, which in turn may be immobilized more efficiently to a support material at said wavelength than a stretch of only one base type composed of cytosine or adenine (see also Example 1 and FIG. 2).

Nucleic acids of only one basetype in accordance with a further preferred embodiment of the invention may have a length from about 2 to about 200 nucleotides, more preferably from about 2 to about 100 nucleotides, particularly preferably from about 2 to about 50 nucleotides. Also preferred is a length of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. A more preferred range is 10-20 nucleotides. Most preferred is a length of 16 nucleotides.

The nucleic acid to be immobilized on the support material may according to a further preferred embodiment be represented by the formula I:

$$5'-Y_n-X_m-B_r-X_p-Z_q-3'$$

In formula I Y and Z are stretches of nucleotides of only one basetype, wherein Y and Z can be of the same or of a different basetype; X is a spacer; B is a sequence of more than one basetype and n, m, r, p and q are numbers of nucleotides in the nucleic acid, for which the following conditions may apply: n, m, p, q, r>1; n, m, r>1 and p, q=0; p, q, r>1 and n, m=0; n, q, r>1 and m, p=0; n, r>1 and m, p, q=0; q, r>1 and n, m, p=0. The term "stretch of nucleotides of only one basetype" has already been defined herein above and relates to nucleotides composed of only one kind of base, e.g. thymine, guanine, adenine, cytosine or uracil or any functional equivalent derivative thereof.

Preferably, the stretches Y and/or Z may be used for immobilization of the nucleic acid due to the presence of nucleotides of only one basetype. More preferably, the stretches Y and/or Z may be composed of guanine or uracil or thymine, more preferably of guanine.

Y and Z may be present at the same time on the same nucleic acid molecule. Such a format may be used for a simultaneous crosslinking via the stretches of only one basetype at both termini of the molecule. In a further preferred embodiment Y and Z may be composed of different basetypes, i.e. Y may be, for example, of basetype uracil, whereas Z may be of basetype guanine or vice versa. Such a nucleic acid may, for example, be immobilized at different wavelengths, preferably at 365 nm and 254 nm, and accordingly lead to a distinguishable orientation of the nucleic acid. Such nucleic acids may also be used for testing of influences of the nucleic acid orientation and immobilization approach on the capability of forming complexes with a complementary oligonucleotide in accordance with the present invention.

In a preferred embodiment Y and Z may be identical in length or may be different in length. Y and/or Z may have a length of about 2 to about 100 nucleotides, more preferably of about 4 to about 50 nucleotides, even more preferably of about 8 to about 30 nucleotides. Also preferred is a length of 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. More preferred is a range of 10-20 nucleotides. Most preferred is a length of 16 nucleotides.

In a format which comprises elements Y and Z at both termini the nucleic acid molecule comprises in its center a region of specific nucleotides B as depicted herein above in formula I. Alternatively, region B may be connected to only one of Y or Z and thus be located at the terminus of the molecule. The region B may be used for specific detection reactions in a classical hybridization or microarray approach, i.e. for interaction reactions with oligonucleotides which specifically bind to their complementary region residing within element B. The length and chemical nature of Y and/or Z may have an influence on the flexibility of zone B and, hence, may be used in order to optimize the specific interaction within this zone, e.g. the specific hybridization reactions using complementary oligonucleotides. In a preferred embodiment B has a length of about 4 to about 90 nucleotides, more preferably a length of about 4 to about 50 nucleotides, even more preferably of about 20 to about 30 nucleotides. Preferred lengths are also 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. Most preferred is a length of 25 nucleotides. Thus, the stretch of nucleotides of only one basetype as defined herein above may be located in accordance with a particular embodiment of the present invention at either of both termini of the nucleic acid molecule, i.e. at either the 3' or the 5' of the immobilized nucleic acid. More preferably the stretch of nucleotides of only one basetype may be located at the 5' end of the nucleic acid molecule.

Element(s) X of Formula I of the present invention may additionally be present as spacer element(s), i.e. as regions comprising sequences of undefined nature. More preferably element X may be composed of abasic nucleotides. The term "abasic" relates to positions in the nucleic acid molecule, at which nor basic residue is present. Abasic regions or stretches of a nucleic acid are, thus, only composed of sugar phosphate backbone elements. Such an abasic structure may have a positive influence on the flexibility of the entire molecule, in particular with respect to element B of the molecule. The inventors could show that the presence of abasic sites have a positive influence on the capability of the immobilized molecule to specifically interact with or hybridize to a target probe (see Example 4 and FIG. 5). A separation of the portions of the molecule used for immobilization, e.g. Y or Z of formula I, form the portion(s) of the molecule used for specific hybridization, e.g. B of formula I, by way of introducing spacer elements comprising abasic sites may significantly decrease unspecific hybridization reactions in the portion of the molecule used for specific hybridization, e.g. B of formula I.

Spacer elements Xm and Xp may entirely be composed of abasic sites or partially be composed of abasic sites. Is the spacer element partially composed of abasic sites the basic portions of the spacer element may be composed of nucleotides of only one basetype or may be composed of nucleotides of different basetypes. Abasic sites as defined herein above may either be accumulated in one stretch or be dispersed within a spacer element or, alternatively, also be present throughout the entire molecule as depicted in formula I. Preferably, the abasic sites are located within the spacer elements X and are accumulated in 1 or 2 stretches.

Preferably, the number of abasic sites within a molecule as depicted in formula I may be between about 1 and about 30, more preferably between about 1 and about 20, even more preferably such a molecule may comprise 1, 2, 3, 4, 5, 6, 7, 8, 9, 10, 11, 12, 13, 14, 15, 16, 17, 18, 19 or 20 abasic sites.

Spacer elements Xm and Xp may be identical in chemical nature and length or may be different in chemical nature and length. Preferably, spacer elements Xm and Xp are of an equal length of about 1 to about 50 nucleotides, more preferably of a length of 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 nucleotides. In a further embodiment, in case q=0, i.e. no sequence element Z as depicted in formula I is present, also a terminal spacer is avoided, i.e. p=0. Similarly, in case n=0, i.e. no sequence element Y as depicted in formula I is present, also a terminal spacer is avoided, i.e. m=0.

The nucleic acid to be immobilized may according to a further embodiment of the invention comprise one or more labels at either or both of the termini, preferably at the 5' terminus. Alternatively, said nucleic acid molecules may also comprise one or more labels at any position throughout the molecule. Preferably said nucleic acid molecule comprises between 1 and 10 labels, which may either be identical or different or any combination thereof. More preferably, the nucleic acid molecule or oligonucleotide comprises between 1 and 5 labels, even more preferably 2 labels and most preferably only one label.

Said labels may be radioactive, fluorescent or chemiluminescent labels. The term "radioactive label" relates to labels emitting radioactive radiation, preferably composed of radioactive isotopes. The term "radioactive isotope" in the context of the label relates to any such factor known to the person skilled in the art. More preferably, the term relates to N-15, C-13, P-31 or I-131.

The term "fluorescent label" relates to chemically reactive derivatives of a fluorophores. Typically common reactive groups include amine reactive isothiocyanate derivatives such as FITC and TRITC (derivatives of fluorescein and rhodamine), amine reactive succinimidyl esters such as NHS-fluorescein, and sulfhydryl reactive maleimide activated fluors such as fluorescein-5-maleimide. Reaction of any of these reactive dyes with another molecule results in a stable covalent bond formed between a fluorophore and a labeled molecule. Following a fluorescent labeling reaction, it is often necessary to remove any nonreacted fluorophore from the labeled target molecule. This may be accomplished by size exclusion chromatography, taking advantage of the size difference between fluorophore and labeled nucleic acid or oligonucleotide. Fluorophores may interact with the separation matrix and reduce the efficiency of separation. For this reason, specialized dye removal columns that account for the hydrophobic properties of fluorescent dyes may be used. A particular advantage of fluorescent labels is that signals from fluorescent labels do not disperse. The lack of dispersal in the fluorescent signal permits, for example, a denser spacing of probes on a support. Another advantage of fluorescent probes is that an easy multiple-color hybridization detection may be carried out, which permits direct quantitative determination of the relative abundance of oligonucleotides forming a complex with the nucleic acid molecules immobilized on the support material. In a particularly preferred embodiment the fluorescent labels FITC, Fluorescein, Fluorescein-5-EX, 5-SFX, Rhodamine Green-X, BodipyFL-X, Cy2, Cy2-OSu, Fluor X, 5 (6) TAMRA-X, Bodipy TMR-X, Rhodamine, Rhodamine Red-X, Texas Red, Texas Red-X, Bodipy TR-X, Cy3-OSu, Cy3.5-OSu, Cy5, Cy5-Osu, Alexa fluors, Dylight fluors and/or Cy5.5-OSu may be used. These labels may be used either individually or in groups in any combination.

The term "chemiluminescent label" relates to a label which is capable of emitting light (luminescence) with a limited emission of heat as the result of a chemical reaction. Preferably, the term relates to luminol, cyalume, oxalyl chloride, TMAE (tetrakis (dimethylamino) ethylene), pyragallol, lucigenin, acridinumester or dioxetane.

Generally, the amount of energy used for an irradiation or crosslinking approach is a parameter of importance. Typically, a person skilled in the art would be able to determine a suitable and optimal irradiation dose by following the indications provided by the manufacturers of irradiation equipment. For instance, the total dose to be applied onto the substrate may be calculated with the formula $D=P \cdot T$, wherein D is the total dose applied onto the substrate in $mJ/cm^2$, P is the power of the light as applied on the support material in $mW/cm^2$ and T is the time during which the dose is applied in seconds. The power of the light as applied on the support material depends on the light source and the distance between the light source and the support material to be irradiated. Crosslinking used for the immobilization of one or more nucleic acids on a solid support at a wavelength of about 300 to about 500 nm in accordance with another preferred embodiment of the present invention may be carried out by using an amount of energy ranging from about 0.5 to about 15 $Joule/cm^2$, more preferably from about 2.0 to about 12 $Joule/cm^2$ even more preferably from about 4 to about 10 $Joule/cm^2$ and most preferably at 5 $Joule/cm^2$. In a particularly preferred embodiment crosslinking is carried out at a wavelength of 365 nm by using an amount of energy of 5 $Joule/cm^2$. The distance between the used light source and the support material may be suitably adjusted according to parameters known to the person skilled in the art. Preferably a distance between 5 cm and 1 m is used, more preferably between 10 cm and 500 cm, even more preferably a distance between 10 cm and 200 cm. Further preferred is a distance between 25 cm and 150 cm. Most preferred is a distance of 50 cm.

The support material in accordance with another preferred embodiment of the present invention may be a solid material or a substrate comprising functional chemical groups, preferably amine groups or amine-functionalized groups. The term "amine-functionalized group" relates to groups which have been functionalized with amines, i.e. which have adopted by chemical modification the function of amines. These amines or amine groups may be primary or secondary amines.

Preferably, the presence and number of functional chemical groups on or inside the support material may be controlled and adjusted via suitable chemical activation processes. Such activation processes may, for instance, provide specifically localized functional groups on or within a support material and facilitate a specific interaction between the nucleic acids and the material within the context of these localized functional groups.

A typical reaction partner for a nucleic acid molecule comprises moieties which are capable of binding to nucleic acids, preferably to amine-functionalized nucleic acids. Examples of such support material are aldehyde, epoxy or NHS substrates. Such material is known to the person skilled in the art. Functional groups, which impart a connecting reaction between nucleic acid molecules which are chemically activated by the introduction of an amine group and a support material are known to the person skilled in the art.

Alternatively a reaction partner for a nucleic acid molecule may be chemically activated, e.g. by the introduction of functional groups, into the support material. The term "activated support material" relates to a material in which interacting or reactive chemical functional groups were established or enabled by chemical modification procedures as known to the person skilled in the art. For example, substrate comprising carboxylate groups has to be activated before use.

The presence and number of functional group on or inside the support material may also have an influence on the orientation and freedom of the immobilized nucleic acids. For example, the presence of a higher number of functional groups may lead to an immobilization at different points within the nucleic acid molecule. Furthermore, the presence of corresponding reactive elements within the nucleic acid molecule may be used for a control of the orientation of the nucleic acid molecule on the support material, e.g. an immobilization at the head or tail region or the 5' or 3' region of the nucleic acid molecule or an immobilization at the centre region alone or at the centre and the end regions at the same time.

The specific positioning of functional chemical groups within the support material may be used in order to facilitate a specific interaction between the nucleic acids and the material within the context of these localized functional groups. Such positioning process may be used in order to provide an ordered array of specifically positioned nucleic acid molecules, e.g. via the use of liquid spotting equipment, preferably ink jet devices. Reactive chemical elements on or within the support material may also be masked by a blocking reagents and become available for interaction with nucleic acid molecules after a de-blocking or de-masking procedure. Alternatively, such chemical elements may be activated by applying corresponding and suitable activation reagents known to the person skilled in the art.

The support material or substrate may additionally comprise photoactivatable compounds which may be used for an interaction between the support material and the nucleic acid molecules. Suitable photoactive chemicals, as known to the person skilled in the art, can be used as connector molecules. Examples of such molecules are photobiotin, or reactive moieties like succinimidyl-6-[4'-azido-2'-nitrophenylamino]hexanoate into the support material.

Photobiotin is composed of a biotinyl group, a linker group, and a nitrophenyl azide group which is photoactivatable. It is generally used for patterning molecules onto solid substrates. Typically, UV lasers stimulate photobiotin to attach various surfaces. The attachment procedure normally takes place in aqueous solutions. Photobiotin is a biotin species, which is photoactivatable and can be used to biotinylate nucleic acids and molecules, in particular those which do not have amine or sulfhydryl groups present to engage in coupling. When exposed to strong light, biotin's aryl azide groups are converted to an aryl nitrene, which is extremely reactive. This process can be used to label a molecule with biotin, e.g. nucleic acid molecules.

The above mentioned compounds may react with the nucleic acid molecules and immobilize the molecules on the substrate after activation by light of the wavelength of about 300 nm to about 500 nm.

In a further preferred embodiment, the support material comprises psoralen. Psoralen is a bifunctional photochemical crosslinking reagent for nucleic acids. It intercalates within nucleic acid helices, and upon irradiation with long-wavelength UV-light (e.g. of a wavelength of 365 nm) forms covalent bonds to pyrimidine bases.

A preferred support material is a porous support material or porous substrate. Particularly preferred is nylon, e.g. Nytran N® or Nytran SPC® or Biodyne C®. A further preferred support material or substrate type is a non-porous substrate. Particularly preferred among non-porous substrates are glass, poly-L-lysine coated material, nitrocellulose, polystyrene, cyclic olefin copolymers (COCs), cyclic olefin polymers (COPs), polypropylene, polyethylene and polycarbonate.

Nitrocellulose membranes are the traditional membranes which are generally used fort transfer techniques like Southern blotting. Methods to achieve nucleic acid binding to nitrocellulose, usually by means of physical adsorption, are widely known form the prior art. The principal advantages of nitrocellulose are its ready availability and familiarity. The use of nitrocellulose membranes with radioactive methods of signal detection is well established.

As an alternative to nitrocellulose membranes nylon may be used as a substrate for nucleic acid binding owing to its greater physical strength and binding capacity, and the wider range of available surface chemistries offered, which optimizes nucleic acid attachment. Immobilization on nylon membranes can be performed, for example, via crosslinking by light, in particular UV-crosslinking, or chemical activation. Immobilization on nylon has been demonstrated to be very durable during repeated probe stripping.

The means by which macromolecules bind to bulk material like, for instance, polystyrene is not well understood. An allocation of binding capacity for bulk materials or its enhancement may be achieved by the provision of functional groups, preferably amine groups, which are made available, e.g. by a coating process or surface treatment or spraying etc. A preferably used coating material is poly-L-lysine, which belongs to the group of cationic surfactants. It contains positively charged hydrophilic (amino) groups and hydrophobic (methylene) groups and is known to interact with nucleic acid molecules.

As bulk material any suitable material known to the person skilled in the art may be used. Typically, glass or polystyrene is used. Polystyrene is a hydrophobic material suitable for binding negatively charged macromolecules because it normally contains few hydrophilic groups.

For nucleic acids immobilized on glass slides, it is furthermore known that by increasing the hydrophobicity of the glass surface the DNA immobilization may be increased. Such an enhancement may permit a relatively more densely packed formation.

In addition to a coating or surface treatment with poly-L-lysine, bulk material, in particular glass, may be treated by silanation, e.g. withepoxy-silane or amino-silane or by silynation or by a treatment with polyacrylamide.

In a further specific embodiment of the present invention bulk material may also be covered with or coated with membrane material as mentioned herein above.

A further aspect of the invention concerns a method for the analysis of a nucleic acid immobilized according to the method as described herein above, which comprises firstly the a hybridization of immobilized nucleic acids with at least one polynucleotide hybridization probe comprising a segment which is complementary to a region of said immobilized nucleic acid and at least one nucleic acid hybridization probe comprising a segment which carries a single mismatch in comparison to a region of said immobilized nucleic acid; and/or a least one nucleic acid hybridization probe comprising a segment which carries a double mismatch in comparison to a region of said immobilized nucleic acid and/or a least one nucleic acid hybridization probe comprising a segment which carries a higher number of mismatches; and secondly the determination of a melting point of the hybrids which have been formed between the immobilized nucleic acid and said hybridization probe(s), wherein the melting point is correlated with the type and/or number of mismatches present in the nucleic acid hybridization probe and the number of nucleotides of only one basetype within the stretch of nucleotides of only one basetype. Typically, a melting curve analysis is performed in order to allow a differentiation between perfect matches and mismatches in nucleic acids. The quality and degree of selectivity of a corresponding differentiation assay depends largely on the features and components used for the melting curve analysis. For example, the quality of nucleic acids, in particular the absence of mismatches in comparison to a known complementary sequence or the absence of structural impairments and problems within the immobilized nucleic acids may be determined by such an analysis.

Alternatively, in a clinical testing setup the target sequences, which are, e.g., derived from potential pathogens, may have a very high degree of homology or identity. In such a situation, a melting curve analysis may help to discriminate between perfect match and mismatch, i.e. it may facilitate a distinction between these very similar species and, thus provide a correct diagnosis of the species in the sample.

The length of nucleic acid molecules to be used as hybridization probes varies depending on the length of the immobilized nucleic acid which is analyzed. Preferably, these nucleic acid molecules have a length of about 2 to about 50 nucleotides, more preferably of about 4 to about 30 nucleotides. Even more preferred are nucleic acid molecules comprising 5, 6, 7, 8, 9, 10, 11, 12, 13, 14, 15, 16, 17, 18, 19, 20, 21, 22, or 24 nucleotides.

The term "higher number of mismatches" preferably relates to a number between 3 and 20 mismatches. The actual number of mismatches is variable and depends on the length of the nucleic acid molecules to be used as hybridization probes as well as the length of the immobilized nucleic acid which is analyzed.

The term "type of mismatches" as used in the context of the above described method for the analysis of an immobilized nucleic acid relates to nature of the mismatches, i.e. which bases are paired or forced to pair. Preferably, the term relates to a G/T, T/G, A/C or C/A mismatch.

The hybridization conditions to be used are standard hybridization conditions as known to the person skilled in the art, e.g. derivable from a molecular biology textbook like Sambrook et al., Molecular Cloning: A Laboratory Manual, 2001, Cold Spring Harbor Laboratory Press. For instance, buffers like SSC or SSPE are used. These buffers are known to the person skilled in the art and can be prepared according to information derivable from, e.g., Sambrook et al., Molecular Cloning: A Laboratory Manual, 2001, Cold Spring Harbor Laboratory Press. SDS (preferably between 0.01-0.5%) may also be added to the buffer. Furthermore, the buffer may comprise blocking agents like herring sperm DNA (hsDNA) or BSA. A preferred buffer comprises 5×SSC, 0.1% SDS, 0.1 mg/ml hsDNA.

The melting points determined according to the method of the present invention may preferably be compared with the melting point values obtained for references or known nucleic acids. Such references may, for example, have been immobilized by different immobilization techniques and/or have been checked for their hybridization behavior in suitable standardized tests as known to the person skilled in the art. More preferably, the references may allow a detailed comparison of melting points with respect to the number of mismatches, the type or nature of mismatches or both parameters in combination.

Usually, the at least one hybridization probe is labeled, e.g. with a label as described herein above, preferably with a fluorescent label. In a more preferred embodiment, detection according to the FRET/Hybprobe principle is performed. In this case, hybridization is performed with two adjacently hybridizing probes each labeled with a different fluorophor, such that FRET can take place, when both probes are hybridized to the target nucleic acid. The term "FRET" means Fluorescence Resonance Energy Transfer. Briefly, a donor chromophore in its excited state can transfer energy by a nonradiative, long-range dipole-dipole coupling mechanism to an acceptor chromophore in close proximity (typically<10 nm). This technique is known to the person skilled in the art.

Typically, melting point values obtained according to the herein above described method are seen as indicative for the selectivity of hybridization or interaction between the immobilized nucleic acid and the hybridization probes. Increasing melting points or temperature normally indicate an increasing selectivity of the binding and are, thus, an evidence for the quality of the immobilized nucleic acids and/or the absence of structural impairments and problems within the immobilized nucleic acids.

A melting point analysis of a nucleic acid immobilized according to the method as described herein above may accordingly be used in order to test and quality control the result of the immobilization procedure. For example, the amount of mismatches in a given nucleic acid molecule may be ascertained.

Furthermore, based on the observation that nucleic acids may be efficiently immobilized to a support by using light of a longer wavelength and that damages to the nucleic acid molecules may consequently be reduced, a melting point analysis as described herein above may advantageously be used in order to optimize the immobilization process, e.g. by determining the optimal or a well working ratio between wavelength of the light, amount of energy to be used for the immobilization and the presence of nucleic acid damages due to the occurrence of mismatch bases or positions.

In a further embodiment, nucleic acid molecules immobilized according to the present invention, preferably after an optimization approach as described herein above, may be used for a melting point analysis. For instance, they may be used for the identification of immobilized nucleic acid-target probe hybrids which perfectly match and do not contain any mismatches. More preferably, they may be used for distinguishing pathogenic bacteria, even more preferably they may be used for distinguishing bacteria of the family of enterobacteriaceae, most preferably, they may be used for distinguishing E. coli from K. pneumoniae.

A melting temperature difference between perfect match and single mismatch of between about 1° C. to 5° C. may be detected with a method for the analysis of a nucleic acid as defined herein above. More preferably, a melting temperature difference between perfect match and single mismatch of about 1 to 2° C. may be detected.

In a further aspect the present invention relates to immobilized nucleic acids, which are obtained or obtainable by the application of the method of the present invention as described herein above. Such immobilized nucleic acids may be present on array structures like microarrays or be deposited freely on membranes or other supports, preferably support material as described herein above. In a particularly preferred embodiment immobilized nucleic acids obtainable by the application of the method of the present invention as described herein above may comprise stretches of nucleotides of only one basetype, more preferably stretches of nucleotides of only one basetype composed of guanine or uracil, even more preferably composed of guanine. Further preferred are such immobilized nucleic acid molecules, which comprise corresponding stretches of nucleotides of only one basetype composed of guanine or uracil or composed of guanine at the termini of the molecule, e.g. either at the 5' or 3' terminus.

The present invention relates in yet another preferred embodiment to the use of nucleic acids which are immobilized according to the method of the present invention as described herein above, for the production of a nucleic acid array. The term "nucleic acid array" relates to a spatial arrangement of nucleic acids, preferably to a gene chip, genome chip, DNA chip, gene array or microarray. A nucleic acid array as provided in the present invention may follow different setups with regard to e.g. the surfaces and/or supports of said arrays. The array setup may be based on glass slides (e.g. following a technique as provided by Affymetrix, Agilent, Nimblegen or CodeLink), on microbeads (e.g. following a technique as provided by Illumina) or on porous membranes (e.g. following a technique as provided by Clondiag, Xceed, Pamgene or Philips).

In the context of the present invention, a nucleic acid array may be provided in the form of a device comprising a chamber suitable for containing liquid samples wherein the liquid sample comprises target nucleic acids. Within such an array probe nucleotides which are immobilized according to the present invention may be positioned at different locations on a surface of the chamber.

The number of immobilized nucleic acid sequences in the microarray devices may be between 5 and 15000, preferably between 5 and 6000, more preferably between 10 and 2000, even more preferably between 20 and 500 and most preferably between 30 and 200. The term "nucleic acid sequence" relates to a sequence which may be represented by at least one up to several thousand nucleic acid molecules comprising a defined nucleotide composition and/or succession. Furthermore, the term may encompass identical or different nucleic acid sequences. The term "different" means that there is at least a difference in one nucleotide position between the sequences. Preferably, the term relates to different sequences.

The term "chamber" of the array defines a closed room wherein the probes are arranged such that immobilized nucleic acids are presented into the defined room such that they are able to contact other molecules present in said room. Of course, said room or chamber may be open for one or more subsequent procedural steps during the experimental process such as, for example, the loading of a liquid sample into said room or a washing or rinsing step. For analyzing interactions between the probes and other molecules present in said room, however, the chamber may be closed to account for a closed reaction system with defined reaction parameters such as the concentrations of certain molecules within said chamber.

In a further preferred embodiment the present invention also relates to the use of a method of immobilization as defined herein above for the production of nucleic acid array, more preferably for the production of nucleic acid arrays as define herein above.

In yet a further preferred embodiment the present invention relates to a diagnostic kit, comprising an array of nucleic acids which are immobilized according to the method of the present invention and a control probe containing a defined amount of a known, labeled nucleic acid complementary to at least one of said immobilized nucleic acids. In a further particularly preferred embodiment the array of nucleic acids is an array as defined herein above.

The term "control probe containing a defined amount of a known, labeled nucleic acid complementary" relates to a well defined nucleic acid or oligonucleotide, which is provided with a label, preferably a fluorescent label, and which is used to calibrate and/or test or quality check at least one of the immobilized nucleic acids present in the form of an array.

In a particularly preferred embodiment, the diagnostic kit according to the present invention may be used for the detection and/or diagnosis of diseases or disorders in animals or plants, preferably in human beings or companion animals, for the detection of genetic variations in individual or populations, for the detection of a predisposition for diseases or disorders in individuals or populations, or for the detection of the presence of resistance genes or cassettes, in particular antibiotic resistance genes or cassettes, in individuals or populations.

The term "detection" relates to the employment of an array of nucleic acids immobilized according to the present invention for interaction or hybridization reactions with nucleic acids or oligonucleotides derived from different sources, tissues, samples, organs etc. linked to the medical or biological identification purposes described herein below.

Preferably, such nucleic acids or oligonucleotides derived from different sources are labeled, e.g. with labels as defined herein above, before they are brought into contact with, or the vicinity of a nucleic acid array as defined herein above in order to allow a recognition of a specific interaction or hybridization between a nucleic acid immobilized in the array and a target nucleic acid derived from any of the above mentioned sources. The preparation and/or processing of such target nucleic acids is known to the person skilled in the art and may be derived, for example, from a textbook like Sambrook et al., Molecular Cloning: A Laboratory Manual, 2001, Cold Spring Harbor Laboratory Press.

Preferably, the diagnostic kit of the present invention may be used for the detection and/or diagnosis of deficiencies or disorders of the immune system, e.g. the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune deficiencies or disorders may be genetic, somatic, such as cancer or some autoimmune disorders, acquired (e.g., by chemotherapy or toxins), or infectious. In another preferred embodiment a kit as defined herein above may be useful in detecting deficiencies or disorders of hematopoictic cells. Examples of immunologic deficiency syndromes include, but are not limited to: blood protein disorders (e.g. agammaglobulinemia, dysgammaglobulinemia), ataxia telangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobinuria.

Moreover, a diagnostic kit of the present invention could also be used to monitor hemostatic or thrombolytic activity. For example, the diagnostic kit may be used to detect blood coagulation disorders (e.g. afibrinogenemia, factor deficiencies) or blood platelet disorders (e.g. thrombocytopenia). Furthermore, the kit may be used to determine parameters indicative for a high risk of heart attacks (infarction) or strokes or detect pre-infarction parameters; such parameter are known to the person skilled in the art.

A diagnostic kit of the present invention could also be used for the detection and/or diagnosis of autoimmune disorders. Examples of autoimmune disorders that can be detected and/or diagnosed include, but are not limited to: Addison's Disease, hemolytic anemia, antiphospho lipid syndrome, rheumatoid arthritis, dermatitis, allergic encephalomyelitis, glomerulonephritis, Goodpasture's-Syndrome, Graves Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitus, and autoimmune inflammatory eye disease.

Similarly, a predisposition for allergic reactions and conditions, such as asthma (particularly allergic asthma) or other respiratory problems, may also be detected and/or diagnosed with a diagnostic kit as defined herein above.

Moreover, the diagnostic kit of the present invention may be used for the detection and/or diagnosis of hyperproliferative disorders, including neoplasms. Examples of hyperproliferative disorders that can be detected include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital. Further examples of hyperproliferative disorders that may be detected by using a kit of the present invention include hypergammaglobulinemia, lymphoproliferative disorders, paraproteinemi as, purpura, sarcoidosis, Sezary Syndrome, Waldenstron's Macroglobulinermia, Gaucher's Disease, histiocytosis, and any other hyperproliferative disease, besides neoplasia, located in an organ system listed above.

The diagnostic kit of the present invention may also be used to detect infectious agents or to detect and/or diagnose infections. Viruses are one example of an infectious agent that can cause diseases or symptoms that can be detected by the diagnostic kit of the present invention. Examples of viruses, include, but are not limited to the following DNA and RNA viral families: Arbovirus, Adenoviridae, Arenaviridae, Arterivirus, Bimaviridae, Bunyaviridae, Caliciviridae, Circoviridae, Coronaviridae, Flaviviridae, Hepadnaviridae (Hepatitis), Herpesviridae (such as Cytomegalovirus, Herpes Simplex, Herpes Zoster), Mononegavirus (e.g. Paramyxoviridae, Morbillivirus, Rhabdoviridae), Orthomyxoviridae (e.g. Influenza), Papovaviridae, Parvoviridae, Picornaviridae, Poxyiridae (such as Smallpox or Vaccinia), Reoviridae (e.g. Rotavirus), Retroviridae (HTLV-I, HTLV-II, Lentivirus), and Togaviridae (e.g. Rubivirus). Viruses falling within these families can cause a variety of diseases or symptoms, including, but not limited to: arthritis, bronchiollitis, encephalitis, eye infections (e.g., conjunctivitis, keratitis), chronic fatigue syndrome, hepatitis (A, B, C, E, Chronic Active, Delta), meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia.

Similarly, the diagnostic kit of the present invention may be used to detect bacterial or fungal agents that can cause disease or symptoms including, but not limited to the following Gram-Negative and Gram-positive bacterial families and fungi: Actinomycetales (e.g. *Corynebacterium, Mycobacterium, Norcardia*), Aspergillosis, Bacillaceae (e.g. Anthrax, *Clostridium*), Bacteroidaceae, Blastomycosis, *Bordetella, Borrelia*, Brucellosis, Candidiasis, *Campylobacter*, Coccidioidomycosis, Cryptococcosis, Dermatocycoses, Enterobacteriaceae (*Klebsiella, Salmonella, Serratia, Yersinia*), *Erysipelothrix, Helicobacter*, Legionellosis, Leptospirosis, *Listeria, Mycoplasmatales*, Neisseriaceae (e.g. *Acinetobacter*, Gonorrhea, Menigococcal), Pasteurellacea Infections (e.g. *Actinobacillus, Heamophilus, Pasteureila*), *Pseudomonas*, Rickettsiaceae, Chlamydiaceae, Syphilis, and Staphylococcal. These bacterial or fungal families can cause the following diseases or symptoms, including, but not limited to: bacteremia, endocarditis, eye infections (conjunctivitis, tuberculosis, uveitis), gingivitis, opportunistic~infections (e.g. AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis, Chlamydia, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g. cellulitis, dermatocycoses), toxemia, urinary tract infections, wound infections.

In a particularly preferred embodiment the diagnostic kit of the present invention may be used to detect the following pathogens or their presence in samples of the human or animal body or samples of human or animal excrementa: *Escherichia coli, Staphylococcus epidermidis, Staphylococcus aureus, Enterococcus faecalis, Klebsiella pneumoniae, Pseudomonas aeruginosa, Enterococcus faecium, Streptococcus pneumoniae, Staphylococcus capitis, Klebsiella oxy-* toca, *Streptococcus agalactiae, Proteus mirabilis, Staphylococcus cohnii, Staphylococcus haemolyticus, Acinetobacter baumannii, Enterococcus* sp., *Proteus vulgaris, Serratia marcescens, Staphylococcus warneri, Staphylococcus hominis, Streptococcus anginosus, Streptococcus mitis, Staphylococcus auricularis, Staphylococcus lentus, Streptococcus* beta haem Group G, *Streptococcus* beta haem Group F, *Streptococcus gordonii, Streptococcus* Group D, *Streptococcus oralis, Streptococcus parasanguis, Streptococcus salivarius, Citrobacter freudii, Listeria monocytogenes, Micrococcus luteus, Acinetobacter junii, Bacillus cereus, Bacteroides caccae, Bacteroides uniformis, Bacteroides vulgatus, Clostridium perfringens, Corynebacterium pseudodiphtheriticum, Corynebacterium* sp., *Corynebacterium urealyticum, Fusiobacterium nucleatum, Micrococcus* sp., *Pasteurella multocida, Propionibacterium acnes, Ralstonia pickettii, Salmonella* ser. Paratyphi B and *Yersinia enterocditi*.

Moreover, the diagnostic kit of the present invention may be used to detect parasitic agents causing disease or symptoms including, but not limited to, the following families: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas. These parasites can cause a variety of diseases or symptoms, including, but not limited to: Scabies, Trombiculiasis, eye infections, intestinal disease (e.g. dysentery, giardiasis), liver disease, lung disease, opportunistic infections (e.g. AIDS related), Malaria, pregnancy complications, and toxoplasmosis, which may also be detected by use of the diagnostic kit of the present invention.

The following examples and figures are provided for illustrative purposes. It is thus understood that the example and figures are not to be construed as limiting. The skilled person in the art will clearly be able to envisage further modifications of the principles laid out herein.

EXAMPLES

Example 1

Testing of Immobilization Efficiency at Different Wavelengths

The immobilization efficiency for different immobilization methods was tested on Nytran SPC nylon membranes. In particular, light at a wavelength of 254 nm, no UV light, and light at a wavelength of 365 nm was used for exposure of nucleic acid molecules during an exposure period of 5 seconds or 20 seconds exposure. As nucleic acid molecules different oligonucleotides comprised of 16 nucleotides of only one basetype (i.e. 16A, 16C, 16G, 16T, 16U), each 16-mer labeled with an Atto655 dye, were used.

The parameter tested was the immobilization efficiency or recovery of the nucleic acids, i.e. the ratio between immobilized oligonucleotides and deposited oligonucleotides, corrected for fluorphore intensity losses during UV application. After UV application, the samples were washed in order to remove the non-bound material. As washing buffer 5×SSC with 0.1% SDS and 0.1 mg/ml herring sperm DNA was used. Washing/blocking was performed during 1 hour at 50° C.

Figure 1:
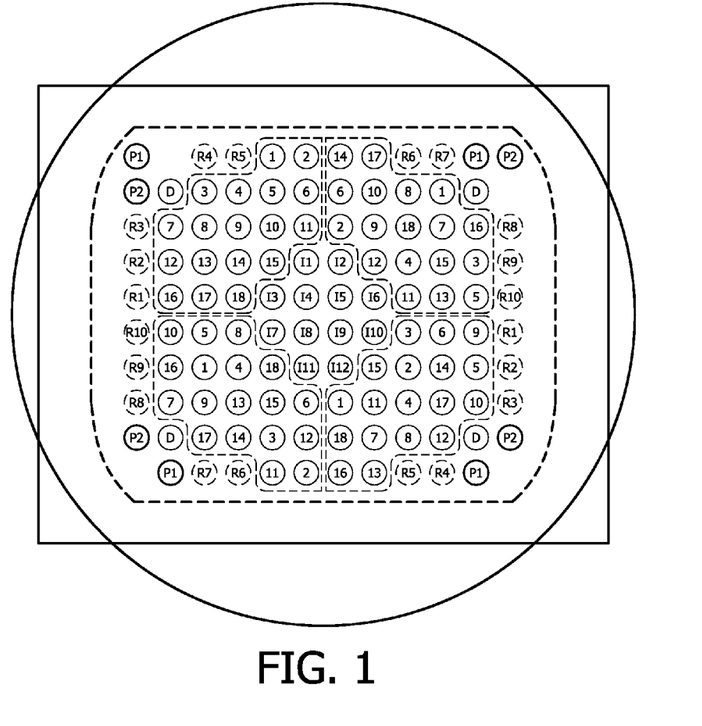
FIG. 1 shows a sample of a dot pattern typical for nucleic acid arrays or spotted microarray.
Figure 2:
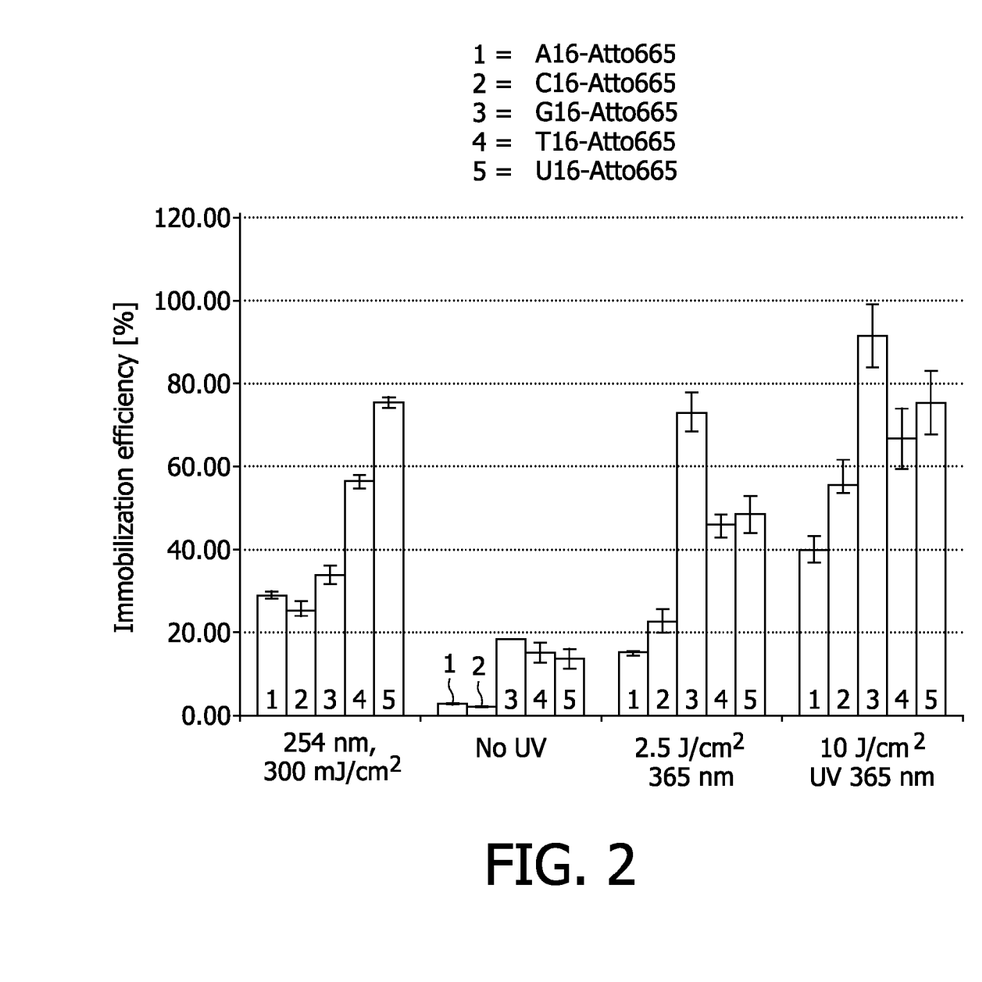
FIG. 2 shows the results of an immobilization efficiency (recovery) assay for different immobilization methods used on Nytran SPC membranes. The following conditions were tested, as indicated on the X-axis: crosslinking at wavelength of 254 nm, no UV, 2.5 Joule/cm$^2$ exposure dose at a wavelength of 320-500 nm and 10 Joule/cm$^2$ exposure dose at a wavelength of 320-500 nm. The bars indicate the recovery of the different oligonucleotides comprised of 16 nucleotides of only one basetype, each 16-mer labeled with an Atto655 dye.

The results of the experiment are shown in FIG. 2. In particular, the bars indicate the recovery of the different oligonucleotides comprised of 16 nucleotides of only one basetype, which can be used for the calculation of the immobilization efficiency.

From FIG. 2 it is clear that for the 254 nm UV exposure, which is traditionally used for UV crosslinking on nylon membranes, the immobilization efficiency is highest when using a U-tail. Also the oligonucleotide comprising of only thymidines performs rather well.

However, when exposing the membranes and oligonucleotides to 300-500 nm UV, particularly to 365 nm, the guanine oligonucleotide outperforms. A different binding mechanism is assumed to be the basis for this crosslinking step. However, the mechanism itself it is not yet fully understood on a molecular level.

Example 2

Recovery Testing and Sensitivity Testing of Nucleic Acids Comprising a T-Tail

The sensitivity, i.e. the number of captured analytes per unit of time, was tested in a real-time hybridization assay. Nytran N or Nytran SPC nylon membranes were used for the experiments.

Figure 3A:
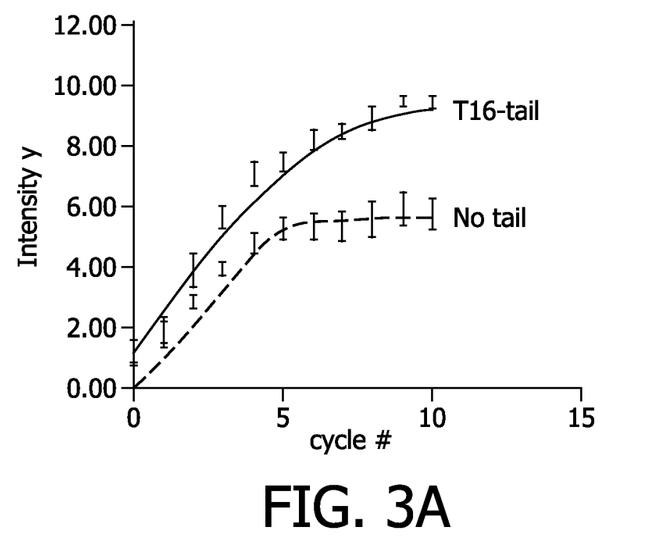
FIG. 3A depicts a real-time hybridization curve of capture oligonucleotides with no T-tail and with a T16-tail, i.e. comprising a stretch of 16 thymidines. The oligonucleotides comprising a T16-tail show increased hybridization signals, which are attributed to a higher recovery.

The assay was carried out with capture oligonucleotides (i.e. deposited nucleic acid molecules to be immobilized) comprising either no T-tail or a T16-tail, i.e. a stretch of 16 thymidines. These experiments were done in a flow cell, which is a device into which the membrane is clamped and the hybridization fluid is pumped through the membrane. In FIG. 3A, on the X-axis, the cycle number is depicted, which is an equivalent for the time (1 cycle takes 1 minute). Hybridization was done with complementary DNA. The hybridization buffer was 5×SSC, 0.1% SDS, 0.1 mg/ml herring sperm DNA. The temperature was set at 50° C.

As can be derived from FIG. 3A the oligonucleotides comprising a T16-tail show increased hybridization signals, which are attributed to higher recovery. The recovery is the ratio between immobilized oligonucleotides and deposited oligonucleotides The experiment shows that the recovery and, in consequence, the sensitivity increases with increasing number of nucleotides of only one basetype within the capture molecule.

Figure 3B:
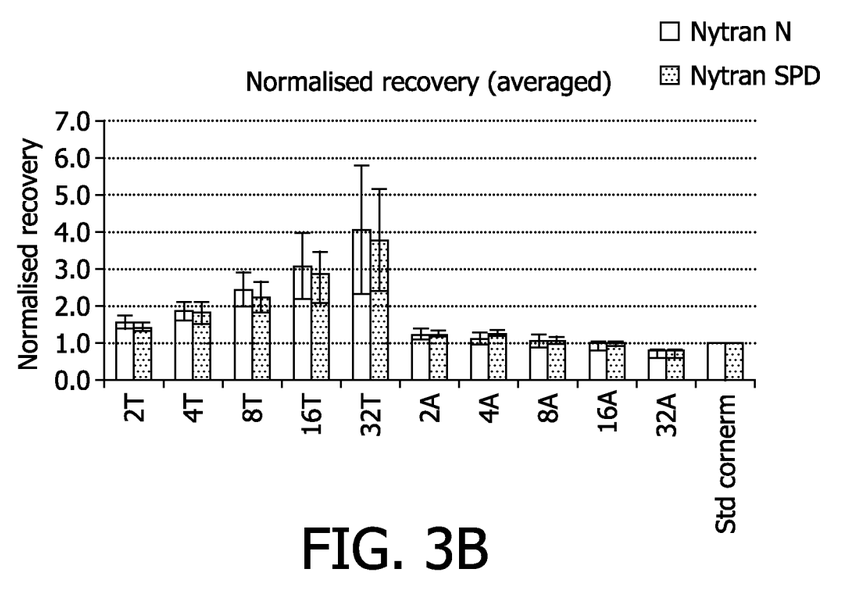
FIG. 3B shows normalized recoveries of deposited capture oligonucleotides comprising T or A nucleotides as a function of the base type (T or A) and the number of bases (2, 4, 8, 16 or 32). It is demonstrated that the recovery can be 3-4 fold increased when the number of T's increases from 2 to 32.

A normalization of the results, as can be derived from FIG. 3B, which shows an averaged recovery rate of deposited capture oligonucleotides comprising T or A nucleotides as a function of the base type (T or A) and the number of bases (2, 4, 8, 16 or 32), makes clear that the recovery can be increased by a factor of 3-4 when the number of nucleotides of only one basetype within the capture oligonucleotide, i.e. the number of Ts, is increased from 2 to 32. The immobilization was carried out by using UV-light of a wavelength of 254 nm.

Example 3

Specificity Testing of Immobilized Nucleic Acids

The specificity of immobilized nucleic acids, i.e. the ability to distinguish between matching and mismatching targets, was tested in a binding assay.

The assay was performed with immobilized nucleic acids (capture probes) comprising 0, 4 or 16 T's. Different capture probes were used that contained perfect match, single mismatch ((AG)mut) and double mismatches((AAGG)mut). Hybridization was done using PCR product. Hybridization was done in a flow cell, which is a device into which the membrane is clamped and the hybridization fluid is pumped through the membrane. The temperature was set at 50° C.

Hybridization was done for one hour. After hybridization, the buffer was changed to 2×SSC and the temperature was increased with 1° C./min in order to make a melting curve and to assess specificity.

Figure 4:
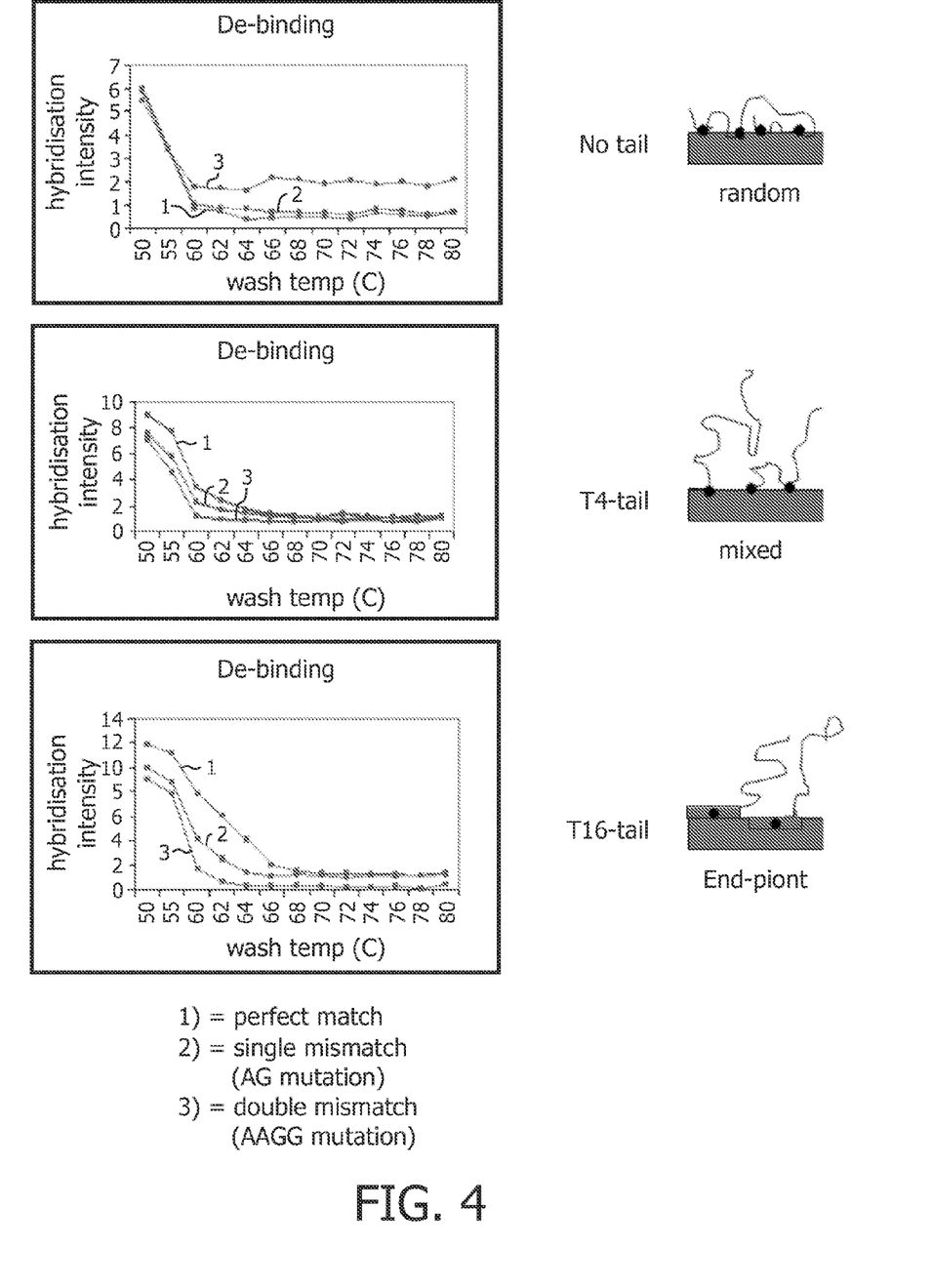
FIG. 4 depicts de-binding curves of complementary, single mismatch ((AG) mutation) and double mismatch ((AAGG) mutation) hybrids for capture probes with 0, 4 and 16 T's. The immobilization of the capture probes is schematically depicted along the graphs. The figure shows that increasing selectivity is obtained due to increased melting temperatures of the complementary probes as compared to mismatch probes.

As can be derived from FIG. 4, which depicts de-binding curves of the complementary, single mismatch and double mismatch hybrids for the different capture probes, an increasing selectivity was obtained due to increased melting temperatures of the complementary probes as compared to mismatch probes.

Example 4

Effect of Abasic Sites on Hybridization Intensity

The effect of abasic sites on hybridization intensity of nucleic acid molecules from DNA with a perfect match and single mismatch ((AG)mut) and double mismatches ((AAGG)mut) was tested in a binding assay. The capture probe comprised 0, 2, 4 or 8 abasic sites. The binding assay was carried out with complementary target oligonucleotides on NytranN nylon membranes.

Figure 5:
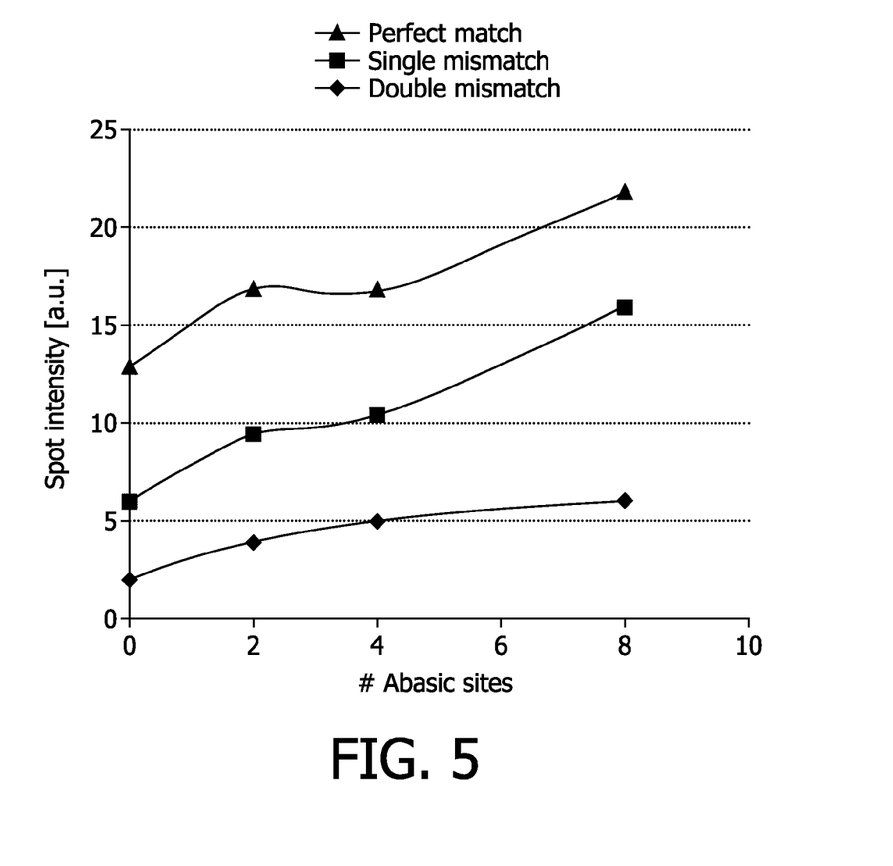
FIG. 5 shows the effect of the number of abasic sites (0, 2, 4, or 8) on the hybridization intensity of amplicons from a bacterial species to complementary as well as mismatch capture-probes.

As can be derived from FIG. 5, the hybridization intensity increased with an increasing number of abasic sites in all tested scenarios, i.e. the hybrisation with complementary target oligonucleotides, mismatch target oligonucleotides or double mismatch target oligonucleotides. The effect is attributable to a more efficient separation of the sequences used for specific immobilization and specific hybridization, which decreases unspecific hybridization.

The invention claimed is:

1. A method for immobilizing nucleic acids on a support, comprising the steps of:
    (a) providing a nucleic acid with a stretch of nucleotides of only one basetype; and
    (b) immobilizing said nucleic acid on a solid support by crosslinking by light, wherein said crosslinking by light is performed at a wavelength of about 300-500 nm and wherein said crosslinking is performed using an amount of energy ranging from about 0.5 Joule/cm$^2$ to about 10 Joule/cm$^2$ and further wherein said nucleic acid includes at least one spacer comprising one or more abasic sites between nucleotides.

2. The method of claim 1, wherein said nucleic acid includes deoxyribonucleic acid (DNA), ribonucleic acid (RNA), peptide nucleic acid (PNA), aminocyclohexylethane acid nucleic acid (CAN), hexitol nucleic acid (HNA), locked nucleic acid (LNA) or arabinoic nucleic acid (ANA); an oligonucleotide thereof; or any combination thereof.

3. The method of claim 1, wherein said nucleic acid is single-stranded.

4. The method of claim 1, wherein said stretch of nucleotides of only one basetype is a stretch of guanines or uracils.

5. The method of claim 4, wherein said stretch of nucleotides of only one basetype has a length from about 7 to about 100 nucleotides.

6. The method of claim 1, wherein said stretch of nucleotides of only one basetype is located at the 3' or 5' terminus of said nucleic acid.

7. The method of claim 1, wherein said nucleic acid is represented by the following formula:

$$5'\text{-}Y_n\text{—}X_m\text{—}B_r\text{—}X_p\text{—}Z_q\text{-}3'$$

with Y and Z being stretches of nucleotides of only one basetype, wherein Y and Z can be the same or of a different basetype; X being a spacer of the at least one spacer including abasic nucleotides; B being a sequence of more than one basetype and n, m, r, p and q being the numbers of nucleotides in the nucleic acid, wherein the following conditions may apply: n, m, p, q, r>1; n, m, r>1 and p, q=0; p, q, r>1 and n, m=0; n, q, r>1 and m, p=0; n, r>1 and m, p, q=0; q, r>1 and n, m, p=0.

8. The method of claim 1, wherein said solid support comprises amine-functionalized groups.

9. The method of claim 1, wherein said solid support comprises primary or secondary amines and/or psoralen.

10. The method of claim 1, wherein said solid support is a porous substrate comprising nylon, or a non-porous substrate comprising glass, poly-L-lysine coated material, nitrocellulose polystyrene, cyclic olefin copolymer (COC), cyclic olefin polymer (COP), polypropylene, polyethylene or polycarbonate.

11. Use of nucleic acids, which are immobilized according to the method of claim 1, for the production of a nucleic acid array.

12. The method of claim 1 wherein the crosslinking by light is performed at a wavelength of 365 nm.

13. The method of claim 5, wherein said stretch of nucleotides of only one basetype has a length of about 16 nucleotides.

14. The method of claim 1, wherein said nucleic acid is double-stranded.

* * * * *